(12) United States Patent
Costantini et al.

(10) Patent No.: US 6,563,001 B1
(45) Date of Patent: May 13, 2003

(54) METHOD FOR SEPARATING AND PURIFYING CARBOXYLIC ACID DERIVED FROM THE DIRECT OXIDATION OF A HYDROCARBON

(75) Inventors: Michel Costantini, Lyons (FR); Eric Fache, Caluire et Cuire (FR); Gilbert Marin, Sainte Foy lès Lyon (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/787,116

(22) PCT Filed: Sep. 14, 1999

(86) PCT No.: PCT/FR99/02182

§ 371 (c)(1), (2), (4) Date: Jun. 12, 2001

(87) PCT Pub. No.: WO00/15598

PCT Pub. Date: Mar. 23, 2000

(30) Foreign Application Priority Data

Sep. 14, 1998 (FR) .............................................. 98 11591

(51) Int. Cl.$^7$ .............................................. C07C 51/31
(52) U.S. Cl. ..................................................... 562/543
(58) Field of Search ......................................... 562/543

(56) References Cited

U.S. PATENT DOCUMENTS 5,463,119 A * 10/1995 Kollar ........................ 562/543

FOREIGN PATENT DOCUMENTS

| DE | 44 28 977 | 2/1996 |
|----|-----------|--------|
| EP | 0 847 980 | 6/1998 |
| FR | 2 092 524 | 1/1972 |
| WO | 99 44980  | 9/1999 |

* cited by examiner

Primary Examiner—Richard L. Raymond
Assistant Examiner—Zachary C. Tucker
(74) Attorney, Agent, or Firm—Burns, Doane, Swecker & Mathis, L.L.P.

(57) ABSTRACT

The present invention relates to an improved process for processing the reaction mixture from the direct oxidation of hydrocarbon into carboxylic acid, using molecular oxygen or a gas containing it, in the liquid phase, in a solvent and in the presence of a catalyst dissolved in the reaction medium, characterized in that the said process comprises:

when the composition of the reaction mixture allows it, a decantation into two liquid phases: a nonpolar upper phase and a polar lower phase;

a distillation of the said lower phase or, where appropriate, of all of the reaction mixture, thus separating, on the one hand, a distillate and, on the other hand, the distillation residue comprising the acids formed, the catalyst, the heavy compounds, at least some of the solvent and, if any, the reaction intermediates and side products;

a purification treatment by oxidation, using molecular oxygen or a gas containing it or using oxygen donors, of the distillation residue obtained above, a distillation of the reaction solvent and the reaction intermediates and side products which may still remain in the mixture, a crystallization of the carboxylic acid produced in the reaction;

a recrystallization from water of the carboxylic acid produced in the reaction.

11 Claims, No Drawings

METHOD FOR SEPARATING AND PURIFYING CARBOXYLIC ACID DERIVED FROM THE DIRECT OXIDATION OF A HYDROCARBON

This application is the national stage of PCT/FR99/02182, filed under 35 U.S.C. 371.

The present invention relates to the processing of the reaction mixture from the direct oxidation of hydrocarbon into carboxylic acid, more particularly the reaction mixture from the oxidation reaction of cyclohexane to adipic acid, and to the separation of the various constituents of the said mixture and to the purification of the carboxylic acid produced in the oxidation reaction.

The direct oxidation of cyclohexane to adipic acid is a process which has been under investigation for a long time, in particular on account of the obvious advantages there would be in converting cyclohexane to adipic acid, in a single step and without using an oxidizing agent such as nitric acid, since this compound generates nitrogen oxides which then need to be processed in order to avoid any pollution.

Patent WO-A-94/07834 describes the oxidation of cyclic hydrocarbons into the corresponding diacids, in a liquid phase comprising a solvent, using a gas containing oxygen and in the presence of an oxidation catalyst such as a cobalt compound, the said solvent comprising an organic acid containing only primary or secondary hydrogen atoms. That patent more particularly develops the phases for processing the final reaction mixture. This processing consists in separating out the diacid formed, cooling the mixture to bring about precipitation of the said diacid, separating the diacid, by filtration, from two liquid phases, a nonpolar phase which is recycled and a polar phase which is also at least partially recycled after an optional hydrolysis, and a separation of a further amount of diacid.

That patent proposes a solution for the one-step oxidation of cyclohexane into adipic acid with industrially acceptable selectivity, but it does not give an industrially acceptable solution to the processing of the reaction mixture from the oxidation, taking into account separation of the various reaction products and side products, the unconverted materials and the catalyst.

In addition, it is found, in practice, that such a concise processing process does not give an adipic acid of the purity required for a great many applications of this highly important starting material.

Specifically, whether it is for the production of polyamide 6-6 or for other applications such as the production of certain polyurethanes, the purity of the adipic acid used must be extremely high, in particular as regards the contents of organic side products which can introduce undesirable colorations.

Patent WO-A-96/03365 describes a more complete process for processing the reaction mixture from the direct oxidation of cyclohexane into adipic acid, as well as the recycling of the catalyst. However, the Applicant has observed that the presence of oxidation intermediates and side products, in particular such as cyclohexanone, cyclohexanol, cyclohexyl esters, hydroxycarboxylic acids and lactones, is liable to interfere with the separation and purification of the adipic acid. The present invention proposes a process which avoids this type of drawback.

More specifically, the invention consists of an improved process for processing the reaction mixture from the direct oxidation of hydrocarbon into carboxylic acid, using molecular oxygen or a gas containing it, in the liquid phase, in a solvent and in the presence of a catalyst dissolved in the reaction medium, characterized in that the said process comprises:

when the composition of the reaction mixture allows it, a decantation into two liquid phases: a nonpolar upper phase essentially containing the unconverted hydrocarbon, and a polar lower phase essentially comprising the solvent, the acids formed, the catalyst and some of the other reaction products and of the unconverted hydrocarbon;

a distillation of the said lower phase or, where appropriate, of all of the reaction mixture, thus separating, on the one hand, a distillate comprising all or at least most of the unconverted hydrocarbon and, on the other hand, the distillation residue comprising the acids formed, the catalyst, the heavy compounds, at least some of the solvent and, if any, the reaction intermediates and side products;

a purification treatment by oxidation, using molecular oxygen or a gas containing it or using oxygen donors, of the distillation residue obtained above, a distillation of the reaction solvent and the reaction intermediates and side products which may still remain in the mixture, a crystallization of the carboxylic acid produced in the reaction;

a recrystallization from water of the carboxylic acid produced in the reaction.

The decantation into two phases of the reaction mixture subjected to the process of the invention depends essentially on the solvent used and the amount of hydrocarbon converted.

The hydrocarbons used as starting materials in the process of the invention are, more particularly, alkanes, cycloalkanes and alkylaromatic hydrocarbons containing from 3 to 20 carbon atoms.

Among these hydrocarbons, cycloalkanes, in particular those which have a ring containing from 5 to 12 carbon atoms, are without doubt the most important, since their oxidation leads to dicarboxylic acids.

The most advantageous hydrocarbon is cyclohexane, oxidation of which leads to adipic acid, one of the base compounds of polyamide 6-6.

For convenience, hereinbelow the invention will be described very generally for the processing of the reaction mixtures from the oxidation of cyclohexane into adipic acid, but the process can also be applied to mixtures obtained from other hydrocarbons, and more particularly from other cycloalkanes.

The cyclohexane phase obtained in the optional decantation step is usually reintroduced into a cyclohexane oxidation operation.

The solvent used in the oxidation of the hydrocarbon, preferably cyclohexane, is an at least partial solvent for the carboxylic acid whose preparation is intended. This solvent can be very varied in nature, provided that it is not substantially oxidizable under the reaction conditions. It can be chosen in particular from polar protic solvents and polar aprotic solvents. Polar protic solvents which may be mentioned, for example, are carboxylic acids which contain only primary or secondary hydrogen atoms, in particular aliphatic acids containing from 1 to 9 carbon atoms, perfluoroalkylcarboxylic acids such as trifluoroacetic acid, water and alcohols. Polar aprotic solvents which may be mentioned, for example, are lower alkyl (=alkyl radical containing from 1 to 4 carbon atoms) esters of carboxylic acids, in particular of aliphatic carboxylic acids containing from 1 to 9 carbon atoms or of perfluoroalkylcarboxylic acids, tetramethylenesulphone (or sulpholane), and aliphatic nitriles such as acetonitrile.

Acetic acid is generally preferred, in particular when the substrate to be oxidized is cyclohexane.

The catalyst preferably contains cobalt, manganese, a mixture of cobalt with one or more other metals such as manganese, chromium, iron, zirconium, hafnium or copper, or a mixture of manganese with one or more other metals such as chromium, iron, zirconium, hafnium or copper. Among the cobalt-based mixtures, catalysts comprising either cobalt and chromium, cobalt, chromium and zirconium, cobalt and iron, cobalt and manganese or cobalt and zirconium and/or hafnium are more particularly suitable. This catalyst is used for the oxidation of cyclohexane in the form of compounds of these metals which are soluble in the reaction medium.

The reaction mixture to be processed by the process of the invention contains, as a guide, on a weight for weight basis, from 1% to 99% of unconverted hydrocarbon, from 1% to 40% of carboxylic acids formed, from 0.1% to 10% of water, from 0.001% to 5% of the metal(s) contained in the catalyst and from 0.1% to 10% of other products of the oxidation reaction, the remainder consisting of the solvent.

The step for distillation of the lower phase or, where appropriate, of the reaction mixture, is carried out such that most, and as far as is possible all, of the unconverted cyclohexane which may still be present in this lower phase is separated from the adipic acid. Some of the reaction intermediates may also be separated out, but these intermediates preferably remain with the diacids formed and the catalyst, as well as with the heavy compounds which may be formed in the initial oxidation reaction of the hydrocarbon. The general term heavy compounds or heavy fraction means the compounds formed which have a boiling point above that of the hydrocarbon and of the reaction intermediates indicated above and which are not the dicarboxylic acids, adipic acid, glutaric acid and succinic acid, formed by the oxidation reaction. This step makes it possible to avoid, during the step for oxidation of the reaction intermediates, such as cyclohexanol, cyclohexanone, cyclohexyl carboxylates, hydroxycarboxylic acids (hydroxycaproic acid) or lactones (essentially butyrolactone and valerolactone), oxidizing a further amount of cyclohexane and consequently forming further reaction intermediates and side products.

The distillation step is generally carried out at a temperature from 25° C. to 250° C. and absolute pressure of between 10 Pa and atmospheric pressure. Preferably, the temperature of the mixture during the distillation will be maintained between 70° C. and 150° C.

To complete the separation of the unconverted cyclohexane, it is possible to use in the distillation an inert entrainer which may be an inert gas such as nitrogen or water vapour.

The distillate obtained in the distillation operation essentially comprises the unconverted cyclohexane, possibly water, and reaction intermediates such as cyclohexanol and cyclohexanone. The cyclohexane and the intermediates are recycled into a further cyclohexane oxidation reaction, after an at least partial removal of the water by any known means, in particular by azeotropic distillation.

The oxidation of the distillation residue (secondary oxidation) is catalysed by the catalyst used in the main oxidation reaction of the hydrocarbon. Taking into account the amounts of reaction intermediates, which are low relative to the amount of hydrocarbon used in the main reaction, the catalyst is in relatively large amount compared with the compounds to be oxidized.

The secondary oxidation can be performed with pure oxygen, with air or with other gaseous mixtures containing oxygen, such as, for example, oxygen-enriched or oxygen-depleted air. It can also be performed with oxygen donors such as, for example, hydrogen peroxide or organic hydroperoxides, such as tert-butyl hydroperoxide, cyclohexyl hydroperoxide or cumyl hydroperoxide.

When the secondary oxidation is carried out with pure oxygen or oxygen in a mixture, the pressure used for this oxidation can vary within a wide range. Generally, the absolute pressure is between 1 bar (0.1 MPa) and 100 bar (10 MPa) and preferably between 5 bar (0.5 MPa) and 50 bar (5 MPa).

The temperature can also vary within a wide range, for example from 25° C. to 250° C. The oxidation is preferably performed at a temperature from 40° C. to 150° C.

After the secondary oxidation step, the solvent and the other liquid compounds which may still be present are distilled off so as to obtain a mixture essentially containing the dicarboxylic acids formed and the catalyst.

A crystallization of the adipic acid is then performed in water or in an organic solvent which at least partially dissolves adipic acid when hot. This organic solvent can be chosen in particular from ketones, carboxylic acids, carboxylic acid esters, alcohols and aliphatic nitriles.

The adipic acid obtained by this crystallization is then recrystallized from water, so as to achieve the purity required for the main applications in which it is used.

The recrystallization may be preceded by a treatment with charcoal to further improve the desired purity.

As may be deduced from the preceding description, the process of the invention makes it possible to obtain pure adipic acid under conditions not requiring an addition catalyst to convert the intermediate compounds and/or the heavy compounds formed in the oxidation reaction of the hydrocarbon. The present process furthermore does not make it necessary to consume an additional reagent such as nitric acid and consequently avoids the corresponding industrial investment.

The examples which follow illustrate the invention.

EXAMPLE 1

A jacketed titanium 1.5 l autoclave fitted with a six-blade turbo mixer and various openings for the introduction of the reagents and the fluids or for removal of the reaction products and the fluids, which have been purged beforehand with nitrogen, is loaded at room temperature with the following:

| | |
|---|---|
| Cobalt acetate tetrahydrate: | 4.0 g (16 mmol) |
| Acetic acid: | 357 g |
| Cyclohexane: | 292.5 g |
| Cyclohexanone: | 3.2 g (32.7 mmol) |

After closing the autoclave, the nitrogen pressure is brought to 20 bar (2 MPa), the stirring (1000 rpm) is started and the temperature is raised to 105° C. over 20 minutes. The nitrogen is then replaced with 20 bar (2 MPa) of depleted air (containing 5% oxygen). The flow rate of inlet gas is adjusted to 250 liters per hour.

After an induction of about ten minutes, during which there is no consumption of oxygen, the temperature rises by 2 to 3° C. and the oxygen begins to be consumed. The inlet oxygen titre is gradually raised to 21%. The oxygen titre at the reactor outlet remains less than 5% throughout the test. The temperature in the autoclave is maintained at about 105° C.

When 53 liters of oxygen have been consumed (degree of conversion of about 20%), continuous injection of the liquid phase is begun: injection of an acetic acid solution containing 1.1% by weight of cobalt acetate tetrahydrate and 1.44% by weight of cyclohexanone at a flow rate of 4.6 ml/min (stabilized regime) and injection of cyclohexane at a flow rate of 5 ml/min (stabilized regime). The liquid product is stored continuously in a 7 liter decanter at 70° C.

After 370 min from the start of the reaction, the air is gradually replaced with nitrogen and the contents of the autoclave are transferred into the decanter. The decanter contains a two-phase mixture. The upper phase, essentially the cyclohexane phase, which contains only a small amount of products and cobalt, is separated out. The lower acetic phase (2668 g) contains most of the oxidation products and the cobalt.

The acetic phase is subjected to a first distillation under the following conditions:

pressure: 60 kPa temperature: 120° C.

The aim of this distillation is to remove all the cyclohexane.

The results obtained are collated in Table 1 below.

TABLE 1

| Compound | Initial untreated mass | Distillation residue 1 |
|---|---|---|
| Cyclohexanone | 281 mmol | 95 mmol |
| Cyclohexyl acetate | 18.5 mmol | 37.2 mmol |
| Free cyclohexanol | 243.4 mmol | 53 mmol |
| Glutaric acid* | 248.6 mmol | 248.6 mmol |
| Succinic acid* | 162.1 mmol | 162.1 mmol |
| Adipic acid* | 2100.8 mmol | 2100.8 mmol |
| Hydroxycaproic acid | 52.0 mmol | 52.0 mmol |
| 3-hydroxyadipic acid | 102.9 mmol | 102.9 mmol |
| Butyrolactone | 87.3 mmol | 58.2 mmol |
| Valerolactone | 33.3 mmol | 12.7 mmol |
| Acetic acid | 1593 g | 430 g |
| Total mass | 2668 g | 895 g |

*Total acid (free and esterified)

The distillate has a mass of 1773 g.

Half of the distillation residue 1 (447.5 g) is subjected to a second, more thorough distillation intended to remove all the volatile organic compounds it contains by means of an injection of water vapour at 150° C. under a pressure of 10 kPa.

The results obtained are collated in Table 2 below.

TABLE 2

| Compound | 447.5 g of the distillation residue 1 to be redistilled | Distillation residue 2 |
|---|---|---|
| Cyclohexanone | 47.5 mmol | negligible |
| Cyclohexyl acetate | 18.6 mmol | negligible |
| Free cyclohexanol | 26.5 mmol | negligible |
| Glutaric acid* | 124.3 mmol | 124.3 mmol |
| Succinic acid* | 81.0 mmol | 81.0 mmol |
| Adipic acid* | 1050.4 mmol | 1050.4 mmol |
| Hydroxycaproic acid | 26.0 mmol | 26.0 mmol |
| 3-hydroxyadipic acid | 51.5 mmol | 51.5 mmol |
| Butyrolactone | 29.1 mmol | negligible |

TABLE 2-continued

| Compound | 447.5 g of the distillation residue 1 to be redistilled | Distillation residue 2 |
|---|---|---|
| Valerolactone | 6.4 mmol | negligible |
| Acetic acid | 215 g | 6.1 |
| Total mass | 447.5 g | 225 |

The distillate has a mass of 222.5 g.

500 g of water are added to the distillation residue 2. The mixture is heated to 70° C. and is then gradually cooled to room temperature (about 20° C.).

After filtration and washing with water, 122 g of crude adipic acid are obtained.

Recrystallization of this crude adipic acid in water gives a purified adipic acid (A) containing:

| | |
|---|---|
| succinic acid: | 0.0003% |
| glutaric acid: | <0.0001% |
| cobalt: | <0.0002% |

The cobalt catalyst is in the crystallization water and the washing water.

EXAMPLE 2

The second half of the distillation residue 1 (447.5 g) of Example 1 is diluted in a further 400 ml of acetic acid and subjected to further oxidation with air.

The 847.5 g of the previous solution are introduced into the 1.5 l titanium autoclave placed under an inert atmosphere of nitrogen. After closing the autoclave, the nitrogen pressure is brought to 20 bar (2 MPa), the stirring (1000 rpm) is started and the temperature is raised to 105° C. over 20 minutes. The nitrogen is then replaced with 20 bar of air. The flow rate of inlet gas is adjusted to 250 liters per hour. After 3 h, the autoclave is cooled to 70° C. and depressurized. The oxidized mass is recovered and subjected to a distillation of type 2 (10 kPa, 150° C., injection of steam).

The results are given in Table 3 below.

TABLE 3

| Compound | 447.5 g of the distillation residue be oxidized | Result of the oxidation | Distillation residue on the oxidized m |
|---|---|---|---|
| Cyclohexanone | 47.5 mmol | negligible | negligible |
| Cyclohexyl acetate | 18.6 mmol | 20 mmol | negligible |
| Free cyclohexanol | 26.5 mmol | 11.2 mmol | negligible |
| Glutaric acid* | 124.3 mmol | 140.2 mmol | 140.2 mmol |
| Succinic acid* | 81.0 mmol | 90.3 mmol | 90.3 mmol |
| Adipic acid* | 1050.4 mmol | 1080.5 mmol | 1080.5 mmol |
| Hydroxycaproic acid | 26.0 mmol | 13 mmol | 13 mmol |
| 3-hydroxyadipic acid | 51.5 mmol | 60 mmol | 60 mmol |
| Butyrolactone | 29.1 mmol | 12.5 mmol | negligible |
| Valerolactone | 6.4 mmol | negligible | negligible |
| Acetic acid | 215 g | 515 | 8.4 |
| Total mass | 447.5 g | 855 | 212 g |

500 g of water are added to the distillation residue 2. The mixture is heated to 70° C. and is then gradually cooled to room temperature (about 20° C.).

After filtration and washing with water, 126 g of crude adipic acid are obtained.

A recrystallization of this crude adipic acid from water gives a purified adipic acid (B) containing:

| | |
|---|---|
| succinic acid: | 0.0002% |
| glutaric acid: | <0.0001% |
| cobalt: | <0.0002% |

The cobalt catalyst is in the crystallization water and the washing water.

The adipic acid batches (A) and (B) are subjected to a heating test.

This test consists in heating 50 g of each batch at 215° C. for 250 min and then placing each of them in 415 ml of aqueous 5% ammonia solution.

The absorbence at 454 nm of the ammonium adipate solutions obtained is then measured.

The results below are obtained, expressed as relative absorbencies, the reference adipic acid (A) representing the value 1:

Adipic acid (A): 1
Adipic acid (B): 0.15

The adipic acid (B) purified according to the present invention contains fewer impurities liable to become coloured on heating.

What is claimed is:

1. A process for processing the reaction mixture from the direct oxidation of hydrocarbon into carboxylic acid, using molecular oxygen or a gas containing it, in the liquid phase, in a solvent and in the presence of a catalyst dissolved in the reaction medium, wherein said process comprises:

decanting when the composition of the reaction mixture allows it, two liquid phases: a nonpolar upper phase comprising the unconverted hydrocarbon, and a polar lower phase comprising the solvent, the acids formed, the catalyst and some of the other reaction products and of the unconverted hydrocarbon;

distilling said lower phase or, where appropriate, all of the reaction mixture, thus separating, on the one hand, a distillate comprising all or at least most of the unconverted hydrocarbon and, on the other hand, the distillation residue comprising substantially all of the acids formed, the catalyst, the heavy compounds, at least some of the solvent and, if any, the reaction intermediates and side products;

purifying by oxidation, using molecular oxygen or a gas containing it or using oxygen donors, the distillation residue obtained above containing substantially all of the acids formed, distilling the reaction solvent and the reaction intermediates and side products which may still remain in the mixture, crystallizing the carboxylic acid produced in the reaction;

recrystallizing from water the carboxylic acid produced in the reaction.

2. The process according to claim 1, wherein the hydrocarbon used as the starting material is selected from the group consisting of alkanes, cycloalkanes and alkylaromatic hydrocarbons having from 3 to 20 carbon atoms.

3. The process according to claim 1, wherein the hydrocarbon comprises cycloalkanes.

4. The process according to claim 1, wherein the solvent used in the oxidation of the hydrocarbon is at least a partial solvent for the carboxylic acid whose preparation is intended and is selected from the group consisting of polar protic solvents and polar aprotic solvents.

5. The process according to claim 1, wherein the solvent comprises aliphatic acids having from 1 to 9 carbon atoms.

6. The process according to claim 1, wherein the catalyst contains cobalt, manganese, a mixture of cobalt with one or more other metals selected from the group consisting of manganese, chromium, iron, zirconium, hafnium and copper or a mixture of manganese with one or more other metals chosen from chromium, iron, zirconium, hafnium and copper.

7. The process according to claim 1, wherein the catalyst comprises either cobalt and chromium, cobalt, chromium and zirconium, cobalt and iron, cobalt and manganese or cobalt and zirconium and/or hafnium.

8. The process according to claim 1, wherein the reaction mixture to be processed comprises, on a weight for weight basis, from 1% to 99% of unconverted hydrocarbon, from 1% to 40% of carboxylic acids produced, from 0.1% to 10% of water, from 0.001% to 5% of the metal(s) contained in the catalyst and from 0.1% to 10% of other products of the reaction, the remainder comprising the solvent.

9. The process according to claim 1, wherein the oxidation of the distillation residue (secondary oxidation) is carried out using molecular oxygen or a gas containing it, at an absolute pressure from 1 bar to 100 bar.

10. The process according to claim 1, wherein the oxidation of the distillation residue (secondary oxidation) is carried out at a temperature from 25° C. to 250° C.

11. The process according to claim 1, wherein the crystallization of the carboxylic acid produced in the reaction is carried out in water or in an organic solvent chosen from ketones, carboxylic acids, carboxylic acid esters, alcohols and aliphatic nitrites.

* * * * *